United States Patent
Frot et al.

(10) Patent No.: US 7,129,471 B2
(45) Date of Patent: Oct. 31, 2006

(54) CORROSION DETECTING DEVICE

(75) Inventors: Didier Frot, St. Germain-En-Laye (FR); Françoise Guillou, Malmaison (FR); Xavier Longaygue, Noisy le Roi (FR)

(73) Assignee: Institut Francais du Petrole, Rueil Malmaison Cedex (FR)

(*) Notice: Subject to any disclaimer, the term of this patent is extended or adjusted under 35 U.S.C. 154(b) by 0 days.

(21) Appl. No.: 10/540,201

(22) PCT Filed: Dec. 4, 2003

(86) PCT No.: PCT/FR03/03594

§ 371 (c)(1),
(2), (4) Date: Jun. 21, 2005

(87) PCT Pub. No.: WO2004/065942

PCT Pub. Date: Aug. 5, 2004

(65) Prior Publication Data

US 2006/0077379 A1   Apr. 13, 2006

(30) Foreign Application Priority Data

Dec. 23, 2002  (FR) .................................. 02 16477

(51) Int. Cl.
*G02B 6/00* (2006.01)
(52) U.S. Cl. .................................... 250/227.14; 385/12
(58) Field of Classification Search .......... 250/227.14, 250/227.19, 227.23, 573, 574; 356/32, 477; 385/12, 13, 37
See application file for complete search history.

(56) References Cited

U.S. PATENT DOCUMENTS

| | | | |
|---|---|---|---|
| 5,200,615 A * | 4/1993 | Hopenfeld | 250/302 |
| 5,367,583 A | 11/1994 | Sirkis | |
| 5,646,400 A | 7/1997 | Perez et al. | |
| 5,708,738 A * | 1/1998 | Perez et al. | 385/37 |
| 6,278,129 B1 * | 8/2001 | Sugasawara et al. | 257/48 |
| 2002/0197026 A1* | 12/2002 | Kato et al. | 385/92 |
| 2004/0165840 A1* | 8/2004 | Kato et al. | 385/92 |
| 2006/0115201 A1* | 6/2006 | Heffels et al. | 385/12 |

OTHER PUBLICATIONS

Database WPI, Section EI, Week 197709, Derwent Publications Ltd., London, GB; AN 1977-B6488Y, XP002255144 & SU 523 295 A (Paperno M B) 2 aout 1976 (August 2, 1976) abrege; figure 1.

* cited by examiner

*Primary Examiner*—Stephone B. Allen
(74) *Attorney, Agent, or Firm*—Antonelli, Terry, Stout and Kraus, LLP.

(57) ABSTRACT

The invention relates to a device for detecting the corrosion induced by a medium on a structure. The device comprises a chamber (5) closed by a closing disc (4) made of such a material that the disc becomes permeable to the medium once corroded by the medium, and means for measuring the refractive index of the medium present in the chamber. According to a preferred embodiment, an optical fiber is used to measure the refractive index variation.

26 Claims, 3 Drawing Sheets

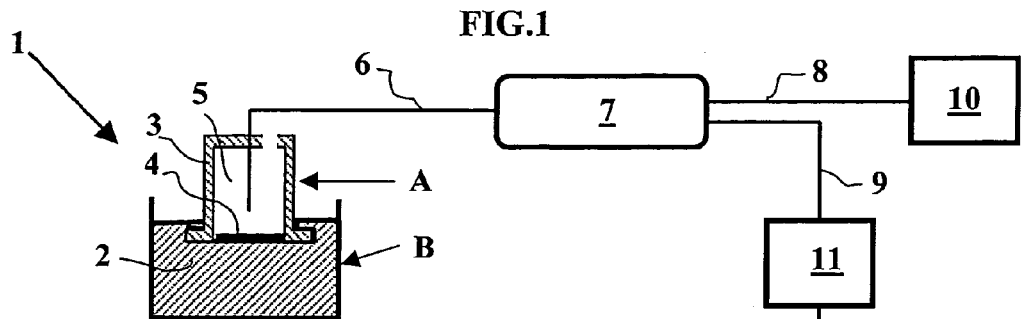
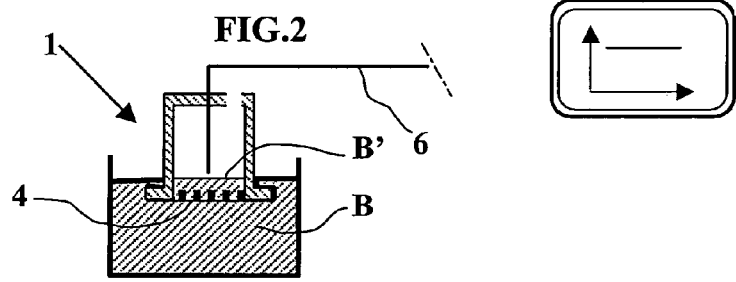
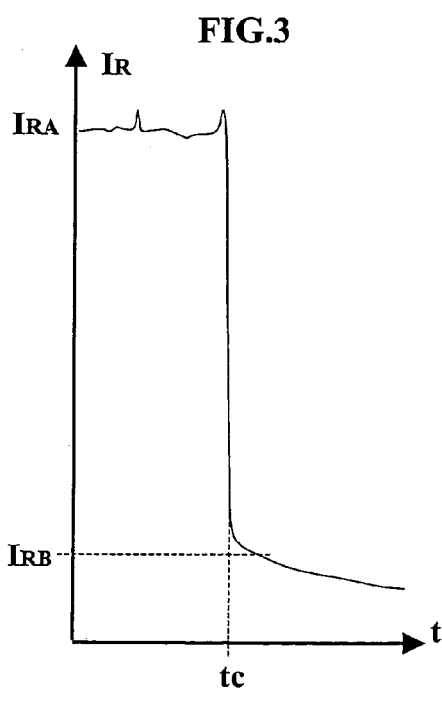
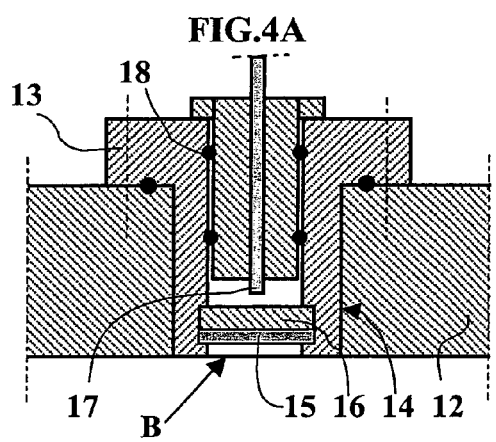
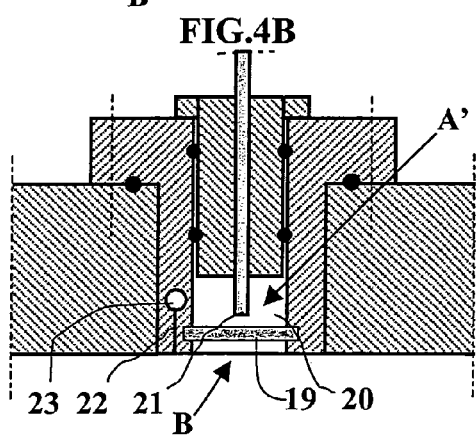

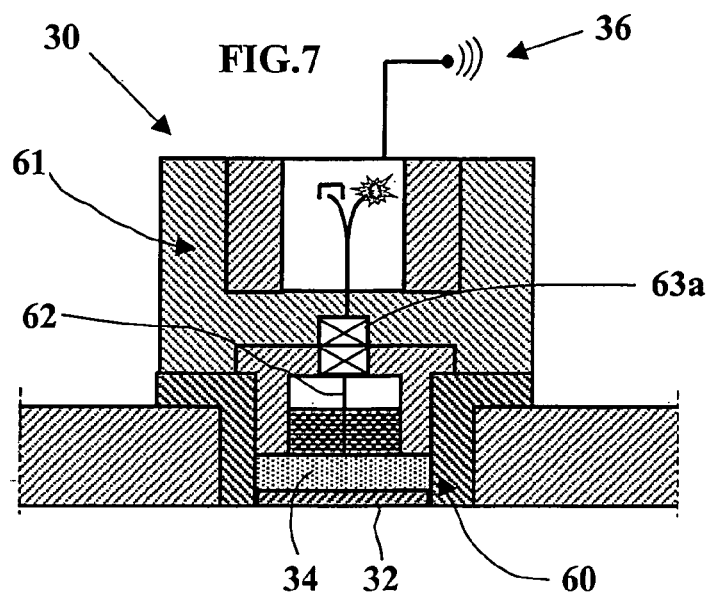
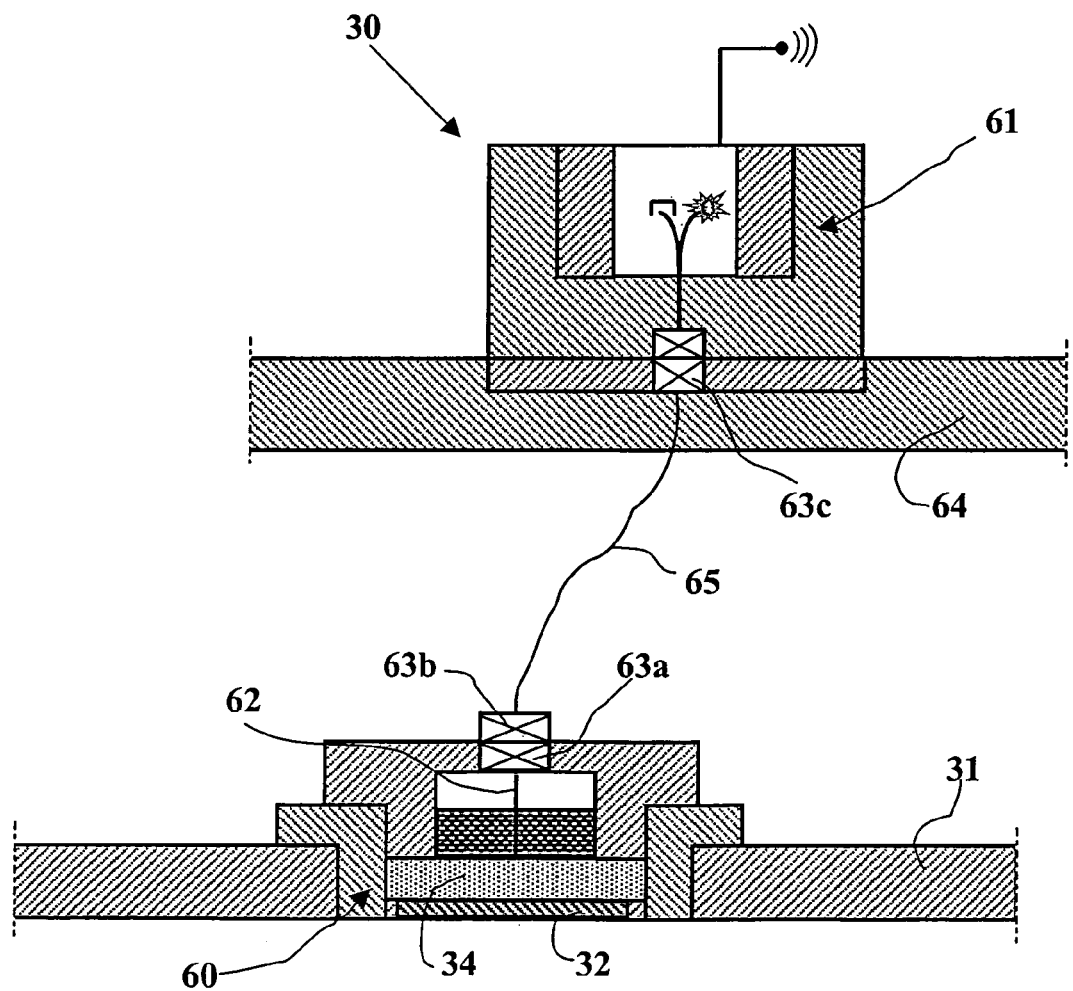

CORROSION DETECTING DEVICE

FIELD OF THE INVENTION

The present invention relates to a corrosion detecting device wherein the measurement of a refractive index is used to obtain and transmit a signal representative of a state of corrosion.

SUMMARY OF THE INVENTION

The present invention thus relates to a device for detecting the corrosion induced by a medium, comprising a chamber closed by a closing disc made of such a material that the disc becomes permeable to the medium once corroded by the medium, and means for measuring the refractive index of the fluid present in the chamber.

The measuring means can comprise a light source and a photodetector.

The refractive index measuring means can comprise at least one optical fiber portion.

One end of the optical fibre can be close to the closing disc.

The chamber may contain air.

The closing disc may be connected to a support withstanding the pressure of the corrosive medium.

The support can be permeable to the medium.

The device can comprise means for balancing the pressure on either side of the disc.

The refractive index measuring means can be included in the chamber.

The device can comprise one of the following measurement transmission mechanism:
  waves (radio, ultrasonic, electromagnetic),
  optical fibre,
  electric conductor.

This invention can advantageously apply for detecting the corrosion of a pipe carrying an effluent, hydrocarbons for example. In a preferred variant, an optical fiber is used.

The present invention combines the advantages of simplicity, precision and easy adaptability to various implementations of devices subjected to corrosion conditions.

BRIEF DESCRIPTION OF THE DRAWINGS

Other features and advantages of the present invention will be clear from reading the description hereafter of non limitative embodiment examples, with reference to the accompanying figures wherein:

FIGS. 1 and 2 diagrammatically show the principle of the device according to the invention;

FIG. 3 shows an example of a record of the signal representative of a corroded state;

FIGS. 4A and 4B show an example of application of the device to a structure under pressure;

FIGS. 7 and 8 illustrate variants according to the invention.

DETAILED DESCRIPTION OF THE INVENTION

Figure 5:
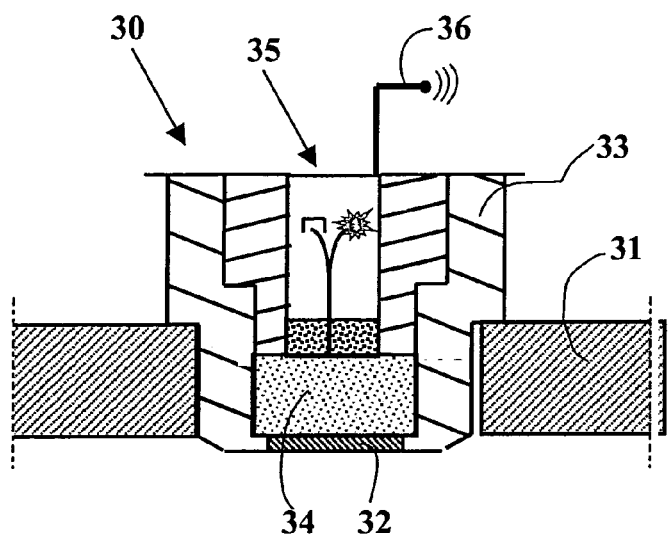
FIG. 5 shows an embodiment variant of the detector according to the invention.

FIG. 1 shows a detector 1 placed in a corrosive liquid 2.0 Detector 1 has a housing 3 closed by a disc 4 separating the inner volume 5 of the housing from the outside, that is the corrosive medium. An optical fiber 6 is inserted in housing 3 so that the end of the fiber is positioned close to disc 4.

Optical fiber 6 is connected to a coupler 7 having two optical fibers 8 and 9, respectively connected to a light source 10 and to a photodetector 11. Light source 10, which may be a laser diode, emits a light ray transmitted by fibers 8 and 6 to medium A present in the inner space of housing 3. Medium A reflects the light ray, according to its own reflection characteristic. The reflected ray is transmitted by means of optical fiber 6 to coupler 7, which guides the reflected light ray to optical fiber 9 connected to a photodetector which may be a photodiode, suited to measure the intensity of the ray reflected by medium A present in the cell. As long as disc 4 is not attacked, or partly destroyed or perforated, by the outer corrosive medium, the intensity of the reflected ray remains constant. The state of preservation of the disc is thus detected, and it can be deduced therefrom that there is no corrosion effect on the disc. Selection of the material of the disc and of its thickness will depend on the desired alarm level in predetermined working conditions under corrosion. Preferably, the material of the disc is the same as the material of the structure subjected to corrosion. The thickness of the disc is preferably selected less than the allowance determined during design of the equipment to take account of the corrosion of the structure.

FIG. 2 shows a diagrammatic partial view illustrating the working principle of the detector. Disc 4 has been corroded by medium B, which has allowed passage of a certain amount of medium B through the disc to reach inner space 5 of the cell. When this amount of medium B' is sufficient, the intensity of the reflected ray changes markedly insofar as the refractive indices of media A and B (or B') are different. The intensity variation of the reflected ray is therefore indicative of a degree of corrosion corresponding to the thickness of disc 4.

FIG. 3 shows a record of the signal received by photodiode Ir as a function of time t. Measurement IrA gives the intensity level of the incident ray resulting from medium A in contact with the end of the optical fiber. At the time tc, disc 4 was perforated under the effect of corrosion by medium B. In the present test, it is a H2SO4 5M solution and the metal disc used is 50-μm thick. After penetration of medium B in contact with the optical fiber, the photodiode measures the intensity IrB of the reflected ray, an intensity that is markedly lower than that of IrA.

FIGS. 4A and 4B diagrammatically illustrate principles of different variants of the detector according to the invention, suited to be used for installations wherein the corrosive fluid is under pressure.

In this case, the corrosion test disc is in direct contact with medium B under pressure. The surface of the disc must therefore withstand this pressure of medium B. Now, for the detection of a corrosion phenomenon to be sensitive enough, the thickness of the disc is generally too thin to intrinsically withstand the pressure. Various systems can be considered:
  the principle of maintenance of the same pressure on either side of the disc for the pressure thereof to be balanced,
  the principle of deposition of the disc on a support withstanding the pressure but sufficiently porous to allow medium B to flow towards the optical fibre once the disc perforated by corrosion.

FIG. 4A illustrates the principle of a detector fastened to wall 12 of a shell containing a corrosive medium B under pressure. The detector is fastened by a flange 13 to a bore 14 in the wall. A disc 15 made of a corrosion-sensitive metal is deposited on a support 16 of such permeability to medium B that, as soon as disc 15 reaches a certain corrosion level (pit, porosity, . . . ), medium B penetrates up to the end of optical fibre 17. At this time, as described above, the refractive index of the medium in which the end of the fibre is located is modified, which informs of the degree of corrosion. Support 16 can be a sintered metal, a perforated disc, or equivalent. The functions of this support are to hold up the disc in contact with a fluid under pressure, while allowing medium B to penetrate up to the end of optical fibre 17 as a result of this perforation by corrosion of disc 15. Of course, seals prevent leakage when the disc is corroded.

FIG. 4B diagrammatically illustrates the principle of a disc 19, thin and therefore of limited pressure resistance, but suitable for determination of a corrosion level. The detector can be mounted as in the embodiment of FIG. 4A. In this case however, chamber 20 in which the end of optical fiber 21 is located is placed under the same pressure as that prevailing in medium B. Chamber 20 is therefore filled with a fluid A' of compressibility close to that of medium B, and placed under pressure by means of a pressure transmission device comprising a line 22 for tapping the pressure in medium B, means 23 (a piston, a membrane for example) for bringing fluid A' under pressure. Thus, the pressure is identical on either side of the disc, which allows a reduced thickness. When the corrosion has reached a determined level through the thickness and the nature of the material which the disc is made of, medium B enters chamber 20 containing fluid A', mixes therewith and causes variation of the refractive index. It is also possible to select a fluid A' undergoing a significant refractive index change as soon as it is polluted by medium B.

FIG. 5 illustrates the principle of a variant of the detector according to the invention. Device 30 is fastened to wall 31 of a structure in contact with the corrosive fluids of medium B. A disc 32 closes the end of body 33 of the detector. A support 34 made of a porous and permeable material holds up disc 32 under the pressure stress of medium B. The body of the detector contains a "capsule" 35 for detecting the refractive index variation. In this figure, the diagrammatic representation of capsule 35 is identical to the representation illustrated in FIG. 6A described below. This capsule comprises measurement transmission means: by electric conductor, optical fiber, waves (radio, ultrasonic, electromagnetic, . . . ) as represented by reference number 36. Thus, the detector can, in a variant, be free of any material transmission link. It will be simple to multiply the number of detectors placed on a structure to manage the corrosion of this structure, for example using discs of different thicknesses in predetermined places, or by arranging them in the same place for local corrosion monitoring.

Figure 6C:
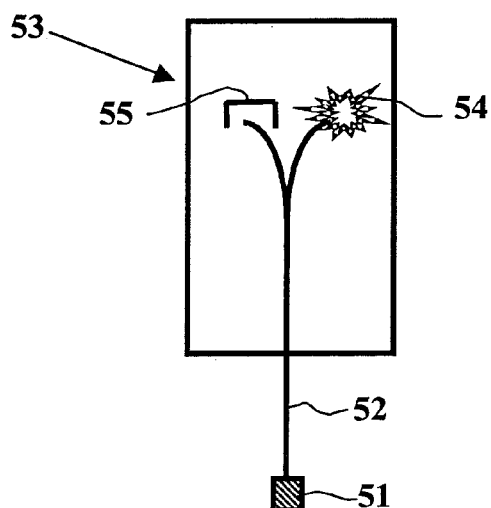
FIGS. 6A, 6B and 6C illustrate working principles of a variant.
Figure 6B:
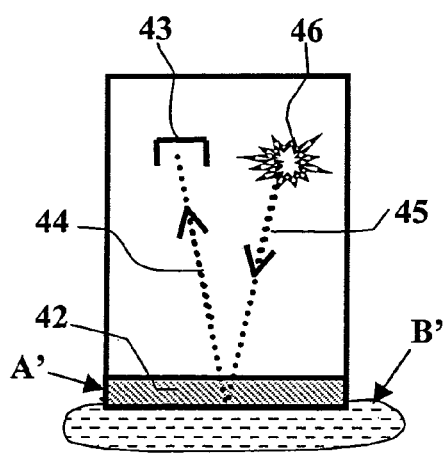
Figure 6A:
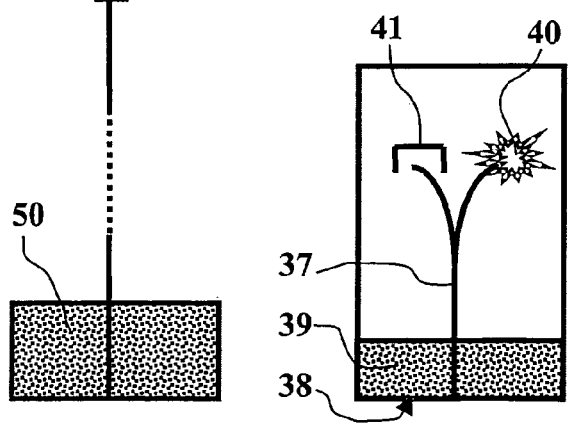

FIG. 6A illustrates a principle of capsule 35 wherein an optical fiber 37 is kept close to base 38 of the capsule by a resin layer 39. A light source (a diode for example) emits a light ray transmitted to base 38 by means of the optical fiber. Base 38 of the capsule is in contact with or in the vicinity of porous material 34 (FIG. 5), or equivalent, so that the fluid of medium B flowing through both corroded disc 32 and porous material 34 leads to a variation in the refractive index at the end of fiber 37. This variation is measured by detector 41 (a photodiode for example). The capsule also comprises electronic means (not shown) for managing and processing the information in order to transmit it to the user, for example by means of waves as illustrated in FIG. 5.

FIG. 6B shows the use of an interface of a medium A' and a medium B' that has entered porous material 34. A detector 43 measures a characteristic of the reflected light ray 44, resulting from an incident ray 45 coming from a light source 46. As in the case of the capsule of FIG. 6A, electronic means inside the capsule manage and transmit the information relative to the refractive index variation of medium B' to the user.

FIG. 6C takes up the principle illustrated by FIGS. 1, 2, 4A and 4B, where the detector contains the end of an optical fiber 50 which is continued by another fiber length 52, connected by means of a connector 51 for example. A measuring capsule 53 contains source 54 and means 55 for measuring the refractive index variation at the end of fibre 50.

FIGS. 7 and 8 illustrate a corrosion detecting device wherein the advantageous possibility of separating the "corrosion" function from the "corrosion measurement" function is used, which allows various embodiments of the present invention.

FIG. 7 illustrates a corrosion detecting device 30 having two parts 60 and 61. Part 60 is fastened to wall 31 of the structure, and essentially comprises corrosion disc 32, disc support, or equivalent, 34, and an optical fiber portion 62 mounted so as to be able to detect a fluid introduced through the disc and to be connected to an optical link by connection means 63a. This part 60 therefore only comprises passive elements.

Part 61 is the measuring and detecting element as such, which comprises connection elements 63b co-operating with connection means 63a of fixed part 60. As described above, this part comprises the light source and the refractive index measuring detector. The information is sent to the user by means 36 or by any other equivalent means.

This embodiment affords the following advantages:— easy change of the active part (measurement, transmission);—use of a single measuring device that is connected, depending on needs, to each fixed corrosion control point.

FIG. 8 is another application of the design principle illustrated by FIG. 7. As in FIG. 7, the same fixed part 60 is installed on a wall 31 of the structure, at the point where corrosion has to be monitored. In the present case, another wall 64 does not allow direct access to part 60 and to connection means 63a for measurement. An optical fiber 65 connected to internal optical fiber 62 runs through second wall 64 and is connected to connection means 63c, accessible on second wall 64. The extension optical fiber 65 can be continuous with internal fiber 62, or cooperate with means 63a through connection means 63b. To carry out control measurements of the state of corrosion of the structure, a measuring part 61 just has to be connected to connection means 63c.

The embodiment according to FIG. 8 is advantageously used in the case of monitoring of structures consisting of double walls: insulated tanks, ship double hulls, . . .

It is also possible to group together all the corresponding optical fibers 65 at all of the corrosion control points, to make their ends (connection means 63c) accessible in a single place such an a control cab for example.

Another application arranges measuring part 61 outside an explosion proof safety area.

The invention claimed is:

1. A device for detecting the corrosion induced by a medium, comprising a chamber closed by a closing disc made of a material such that the disc becomes permeable to the medium once corroded by the medium; and means for measuring a refractive index of fluid present in the chamber.

2. A device as claimed in claim 1, wherein the means for measuring comprises a light source and a photodetector.

3. A device as claimed in claim 1, wherein the means for measuring comprise at least one optical fiber portion.

4. A device as claimed in claim 3, wherein one end of the optical fiber is adjacent to the disc.

5. A device as claimed in claim 1, wherein the chamber contains air.

6. A device as claimed claim 1, wherein the disc is connected to a support withstanding pressure of the medium.

7. A device as claimed in claim 6, wherein the support is permeable to said medium.

8. A device as claimed in claim 1, comprising means for balancing pressure on sides of the disc.

9. A device as claimed in claim 1, wherein the means for measuring is are included in the chamber.

10. A device as claimed in claim 9, comprising at least one of measurement transmission mechanism:
 waves,
 an optical fiber, and
 an electric conductor.

11. A device as claimed in claim 2, wherein the means for measuring comprise at least one optical fiber portion.

12. A device as claimed in claim 11, wherein one end of the optical fiber is adjacent to the disc.

13. A device as claimed in claim 2, wherein the chamber contains air.

14. A device as claimed in claim 3, wherein the chamber contains air.

15. A device as claimed in claim 4, wherein the chamber contains air.

16. A device as claimed in claim 11, wherein the chamber contains air.

17. A device as claimed in claim 12, wherein the chamber contains air.

18. A device as claimed in claim 2, comprising means for balancing pressure on sides of the disc.

19. A device as claimed in claim 3, comprising means for balancing pressure on sides of the disc.

20. A device as claimed in claim 4, comprising means for balancing pressure on sides of the disc.

21. A device as claimed in claim 5, comprising means for balancing pressure on sides of the disc.

22. A device as claimed in claim 13, comprising means for balancing pressure on sides of the disc.

23. A device as claimed in claim 14, comprising means for balancing pressure on sides of the disc.

24. A device as claimed in claim 15, comprising means for balancing pressure on sides of the disc.

25. A device as claimed in claim 16, comprising means for balancing pressure on sides of the disc.

26. A device as claimed in claim 17, comprising means for balancing pressure on sides of the disc.

* * * * *